United States Patent [19]

Kung et al.

[11] Patent Number: 5,446,147

[45] Date of Patent: Aug. 29, 1995

[54] FLUORINATED AND IODINATED DOPAMINE AGENTS

[75] Inventors: Hank F. Kung, Wynnewood; Sumalee Chumpradit, Bryn Mawr; Mei Ping Kung, Wynnewood, all of Pa.

[73] Assignee: Trustees of the University of Pennsylvania, Philadelphia, Pa.

[21] Appl. No.: 862,840

[22] Filed: Apr. 3, 1992

[51] Int. Cl.[6] .............. C07D 223/16; C07D 451/02; C07D 211/56; C07D 207/08

[52] U.S. Cl. ............................. 540/595; 546/124; 546/224; 548/567

[58] Field of Search .............. 548/567; 424/1.1, 1.85, 424/1.89; 514/428, 359; 546/224, 124, 112; 540/595

[56] References Cited

U.S. PATENT DOCUMENTS 5,068,326  11/1991  Kung .................... 540/594

FOREIGN PATENT DOCUMENTS 0156776  10/1985  European Pat. Off. .
0060235  1/1986   European Pat. Off. .
0207913  1/1987   European Pat. Off. ... C07D 207/09
0234872  9/1987   European Pat. Off. .
0393838  10/1990  European Pat. Off. .
WO84/03281 8/1984  WIPO .

OTHER PUBLICATIONS

Chumpradit, S., et al., "Synthesis and Resolution of (±)-7-Chloro-8-hydroxy-1-(3'-iodophenyl)-3-methyl-2,3,4,5-tetrahydro-1H-3-benzazepine (TISCH): A High Affinity and Selective Iodinated Ligand for CNS D1 Dopamine Receptor", J. Med. Chem. 34, No. 3: 877–883 (1991).

Billings, J. J., et al., "Characterization of Radioiodinated TISCH: A High-Affinity and Selective Ligand for Mapping CNS $D_1$ Dopamine Receptor", J. Neurochem 58, No. 1: 227–236 (1992).

Hogberg, T., et al., "New selective dopamine D-2 antagonists as antypsychotic agents Pharmacological, chemical, structural and theoretical considerations", Acta Pharm. Suec. 24: 289–328 (1987).

Halldin, C., et al., "A Comparative PET-Study of Five Carbon-11 or Fluorine-18 Labelled Salicylamides. Preparation and In Vitro Dopamine D-2 Receptor Binding", Nucl. Med. Biol. 18, No. 8: 871–881 (1991).

Hogberg, T., et al., "Potential Antipsychotic Agents. 9. Synthesis and Stereoselective Dopamine D-2 Receptor Blockade of a Potent Class of Substituted (R)--N-[(1-Benzyl-2-pyrrolidinyl)methyl]benzamides. Relations to Other Side Chain Congeners", J. Med. Chem. 34: 948–955 (1991).

de Paulis, T., et al., "22. Quantitatie Structure-Affinity Relationships of Dopamine $D_2$ Receptor Antagonists: A Comparison between Orthopramides and 6-Methoxysalicylamides", Helvetica Chimica Acta 74: 241–254 (1991).

Yue, E. W., et al., "Synthesis of 2,3-Dimethoxy-5-iodobenzoic Acid", J. Org. Chem. 56: 5451–5456 (1991).

Kessler, R. M., et al., "High Affinity Dopamine D2 Receptor Radioligands. 1. Regional Rat Brain Distribtuion of Iodinated Benzamides", J. Nucl. Med. 32 No. 8: 1593–1600 (1991).

(List continued on next page.)

Primary Examiner—Gary Geist
Assistant Examiner—Lara E. Chapman
Attorney, Agent, or Firm—Woodcock Washburn Kurtz Mackiewicz & Norris

[57] ABSTRACT

This invention relates to novel dopamine D-1 and D-2 imaginging agents which are both fluorinated and iodinated and can appropriately labelled for use in both PET and SPECT imaging. Compounds include S-(−)-2-fluoroethoxy-3-methyl-N-[(1-ethyl-2-pyrrolidinyl)methyl]-5-iodobenzamide and R(+)-2,3-dimethoxy-N-[(1-(4'-fluorobenzyl)-2-pyrrolidinyl)methyl]-5-iodobenzamide.

35 Claims, 2 Drawing Sheets

HPLC Chromatogram of FIDA1,(4)

OTHER PUBLICATIONS

Murphy, R. A., et al., "Synthesis and Characterization of Iodobenzamide Analogues: Potential D-2 Dopamine Receptor Imaging Agents", *J. Med. Chem.* 33, No. 1:171-178 (1990).

Kung, H. F., et al., "Current and Future Radiopharmaceuticals for Brain Imaging With Single Photon Emission Computed Tomography", *Seminars in Nuclear Medicine,* vol. XX, No. 4: 290-302 (1990).

Kung, H. F., et al., "In Vitro and In Vivo Evaluation of [$^{123}$I]IBZM: A Potential CNS D-2 Dopamine Receptor Imaging Agent", *J. Nucl. Med.* 30, No. 1: 88-92 (1989).

Kung, H. F., et al., "In Vivo SPECT Imaging of CNS D-2 Dopamine Receptors: Initial Studies with Iodine-123-IBZM in Humans", *J. Nucl. Med.* 31: 573-579 (1990).

Kung, M-P., et al., "The Characterization of IBF as a New Selective Dopamine D-2 Receptor Imaging Agent", *J. Nucl Med.* 31: 648-654 (1990).

Kung, M-P., et al., "A Kit Formulation for Preparation of Iodine-123-IBZM: A New CNS D-2 Dopamine Receptor Imaging Agent", *J. Nucl. Med.* 32: 339-342 (1991).

Hoegberg et al., "Synthesis & Binding Properties of the New Fluorinated Benzamide NCQ616", *Acta Pharm. Nord.* 4(4), pp. 297-300, 1992. (abstract provided in action).

Figure 1. HPLC Chromatogram of FIDA1,(4)

Chiral Column, OD, 10%EtOH/n-Hexane, 1mL/min

Figure 2. HPLC Chromatogram of FIDA2,(6)

FLUORINATED AND IODINATED DOPAMINE AGENTS

FIELD OF THE INVENTION

This invention relates to novel dopamine D-1 and D-2 imaginging agents which are both fluorinated and iodinated for use in PET and SPECT imaging.

BACKGROUND OF THE INVENTION

For the treatment of a wide variety of different nervous and mental diseases, it is desirable to be able to monitor the effectiveness of drugs and substances which affect brain chemistry. For instance, in the treatment of schizophrenia or Parkinson's Disease, it is highly desirable to be able to gauge the biochemical effects of drugs administered for blocking the patient's dopamine receptors. If too little of the drug is administered, the desired blockade does not occur, and if too much of the drug is administered, there can be severe side effects.

New and powerful imaging methods which enable one to assess the living brain in vivo and thereby monitor the effectiveness of drugs and substances that affect brain chemistry have recently been developed. Methods such as positron emission tomography (PET) and single photon emission tomography (SPECT) involve the administration to a patient of radioactive tracer substances comprising a ligand that binds to presynaptic or postsynaptic neuroreceptors in the patient's brain. Emissions (primarily gamma rays which are emitted from the positrons or photons emitted from the radioactive tracer) are measured. These emissions are indicative of the number and degree of occupancy of blocking of the neuroreceptors. The number of neuroreceptors and the degree of occupancy or blocking is calculated utilizing a mathematical model, and compared with an intra-person or inter-person control, to determine the degree of drug response. Further treatment of the patient with drugs is based upon the comparisons made.

It is generally accepted that there are two subtypes of dopamine receptors, designated as D-1 and D-2 receptors. Recent reports have suggested that these two subtypes of receptors exhibit opposite biochemical effects: D-1 agonists stimulate adenyl cyclase activity, while D-2 agonists inhibit the enzyme activity. It is clear that these receptor subtypes influence each other, and yet they display separate and distinct functions on body physiology and biochemistry. Monitoring of both D-1 and D-2 receptors in a patient is important for assessing the dopaminergic system and ultimately assisting patient management.

Numerous benzazepine derivatives which are D-1 receptors have been disclosed. Examples are provided below in Table I.

TABLE I

Dopamine D-1 Receptors

| Compound | $R_1$ | $R_2$ | $R_3$ |
|---|---|---|---|
| SCH-23390 | Cl | H | H |
| SKF-83566 | Br | H | H |
| SCH-23982 | I | H | H |
| IMAB | Cl | $N_3$ | I |
| FISCH | Cl | I | H |

For more detail, see the disclosure of U.S. Pat. No. 5,068,326 to Kung, the disclosure of which is hereby incorporated by reference; Chumpradit, S. et al., *J. Med. Chem.* 34, No. 3, 877–883 (1991); and Billings, J. J. et al., *J. Neurochem* 58, No. 1, 227–236 (1992).

There are also many known examples of dopamine D-2 receptors, such as those illustrated below in Table II.

TABLE II

Dopamine D-2 Receptors

Raclopride ($K_d$ 10 nM)

IBZM ($K_d$ 0.426 nM)

IBF ($K_d$ 0.106 nM)

TABLE II-continued

Dopamine D-2 Receptors

Fluoropropyl-
Epidepride ($K_d$ 0.03 nM)

Epidepride ($K_d$ 0.024 nM)

Ioxipride ($K_d$ 0.019 nM)
NCQ298

For further discussion of these and related D-2 receptors, see the following: European Patent Application No. 393,838, published Oct. 24, 1990, and equivalent to allowed U.S. patent application Ser. No. 339,006, filed Apr. 17, 1989, the disclosure of which is hereby incorporated by reference; Hogberg, T., et al., *Acta Pharm. Suec.* 24, 289-328 (1987); Halldin, C., et al., *Nucl. Med. Biol.* 18, No. 8, 871-881 (1991); Hogberg, T. et al., *J. Med. Chem.* 34, 948-955 (1991); De Paulis, T., et al., *Helvetica Chimica Acta* 74, 241-254 (1991); Yue, E. W. et al., *J. Org. Chem.* 56, 5451-5456 (1991); Kessler, R. M. et al., *J. Nucl. Med.* 32, No. 8, 1593-1600 (1991); Murphy, R. A., et al., *J. Med. Chem.* 33, No. 1, 171-178 (1990); Kung, H. F., et al., *Seminars in Nuclear Medicine*, Vol. XX, No. 4, 290-302 (1990); Kung, H. F. et al., *J. Nucl. Med.* 30, No. 1, 88-92 (1989); Kung, H. F. et al., *J. Nucl. Med.* 31, 573-579 (1990); Kung, M-P. et al., *J. Nucl. Med.* 31, 648-654 (1990); Kung, M-P. et al., *J. Nucl. Med.* 32, 339-342 (1991); European Patent Application 60,235, published Jan. 8, 1986; European Patent Application 156,776, published Oct. 2, 1985; European Patent Application 207,913, published Jan. 7, 1987; PCT Patent Application PCT/GB84/00047 published under publication number WO 84/03281 on Aug. 30, 1984; and European Patent Application 234,872, published Sep. 2, 1987.

In general, it is well recognized that of the two imaging methods, PET and SPECT, PET provides higher resolution, higher sensitivity and better quantitation capability. SPECT imaging, however, offers the advantages of being more readily available, cheaper to perform and of being technically less demanding as it can be performed without the need of an on-site cyclotron. Currently, different dopamine receptor-specific imaging agents are used for PET and SPECT imaging, so data obtained for PET cannot be easily transferred to SPECT, and vice versa. In many cases, the different agents are close analogs, but they are not the same molecule, and pharmacokinetic and metabolic differences prevent their cross comparison. It would therefore be of great use to bridge the gap and to provide a single radiopharmaceutical for both PET and SPECT imaging.

SUMMARY OF THE INVENTION

A series of dual-labeled agents, specific to either D-1 or D-2 dopamine receptors, and which can be used both in PET and SPECT imaging, have now been found. These compounds have the formulas I, II or III as described below:

where

X is selected from the group consisting of I, —($CH_2$)$_n$I and —($CH_2$)$_q$C=CHI;

n is an integer of from one to six;

q is zero or an integer of from one to four;

Y is selected from the group consisting of H and $OR_3$;

Z is selected from the group consisting of H and $OR_2$ or Z and $OR_1$ can be taken together to form a ring where m is an integer of from two to four;

$R_1$, $R_2$ and $R_3$ are independently selected from the group consisting of H, $C_1$-$C_5$ alkyl, and —($CH_2$)$_n$F; provided that, in compounds of Formula I, at least one of $R_1$, $R_2$ and $R_3$ is —($CH_2$)$_n$F, and that, in Compounds of Formula II, at least one of —$OR_1$, Y and Z is —O($CH_2$)$_n$F;

$R_4$ is selected from the group consisting of OH, Cl and $CH_3$;

$R_5$ is selected from the group consisting of H, Cl and $OCH_3$, provided that when $R_4$ is Cl, then $R_5$ is H or $CH_3$, and that when $R_5$ is H or $CH_3$, then $R_4$ is Cl;

A is selected from the group consisting of and s is an integer of from 1 to 3;

W is selected from the group consisting of F and (CH$_2$)$_n$F; and

V is selected from the group consisting of H, OH, OCH$_3$, CH$_3$ and I.

Tests indicate that compounds of Formulas I and II should be useful D-2 dopamine receptor imaging agents for both PET and SPECT imaging, and suggest that compounds of Formula III should be useful D-1 dopamine receptor imaging agents for both PET and SPECT imaging. By using the same molecule for two imaging modalities, one can expect the same pharmacological profile, same toxicology and same pharmacokinetics (to the extent that the biodistribution of the $^{123}$I and $^{18}$F labeled parent compound is the same). These agents should be highly useful for routine clinical use. Tests indicate that the agents demonstrate desired in vitro and in vivo properties indicating the agent is receptor selective (high basal ganglia/cerebellum ratio), that they can be easily radiolabeled, that they exhibit in vivo binding kinetics and metabolic properties suitable for quantitative modeling, that they show acceptable radiation dosimetry, and that they should be useful in a simple and relatively short imaging procedure, allowing for a data acquisition time in minutes.

Compounds of Formulas IV, V and VI, shown below, are useful as intermediates in preparing the radioactive I-labeled imaging agents of this invention:

where

R$_1$, R$_2$, Y, Z, A, R$_4$ and R$_5$ are as defined above and where R$_6$ is a C$_1$-C$_3$ alkyl group.

Compounds of Formulas VII, VIII and IX, shown below, are useful as intermediates in preparing the radioactive F-labeled imaging agents of this invention:

where

Y' is selected from the group consisting of H and OR$_3$'; R$_6$ is a C$_1$-C$_4$ alkyl group; and

R$_1$', R$_2$' and R$_3$' are independently selected from the group consisting of H, C$_1$-C$_5$ alkyl and —(CH$_2$)$_n$OTs where Ts is tosylate, provided that at least one of R$_1$', R$_2$' and R$_3$' is —(CH$_2$)$_n$OTs.

where

Y' is selected from the group consisting of H and OR$_3$';

Z' is selected from the group consisting of H and OR$_2$' or Z' and OR$_1$' can be taken together to form a ring $R_1'$, $R_2'$ and $R_3'$ are independently selected from the group consisting of H, $C_1$–$C_5$ alkyl and —$(CH_2)_n$OTs where Ts is tosylate, provided that at least one of $R_1'$, Y' and Z' is —$O(CH_2)_n$ OTs where Ts is tosylate; and A' is selected from the group consisting of where
$R_4$, $R_5$, and X are as defined above.

This invention, therefore, relates to the compounds of Formulas I, II and III, to methods of using them as imaging agents, to methods of preparing compounds of Formulas I, II and III, and to the novel intermediates of Formulas IV, V, VI, VII, VIII and IX.

DETAILED DESCRIPTION OF THE INVENTION

Compounds of Formulas I and II may be prepared by methods analogous to those shown in Scheme A for the synthesis of the compounds (S)-(—)-2-fluoroethoxy-3-methyl-N-[(1-ethyl-2-pyrrolidinyl)methyl]-5-iodobenzamide (4) (refered to as "FIDA1") and R(+)-2,3-dimethoxy-N-[(1-(4'-fluorobenzyl)-2-pyrrolidinyl)methyl]-5-iodobenzamide (6) (referred to as "FIDA2").

The iodoester 1 was prepared by iodination of the corresponding ester using sodium iodide in the presence of sodium hypochlorite as an oxidant. O-Alkylation of 1 with 1-bromo-2-fluoroethane or methyl iodide, followed by basic hydrolysis, afforded the acid 3 or 5, respectively. Treatment of acid 3 with oxalyl chloride produced the acid chloride, which was reacted with S-(—)-N-ethyl-2-(aminomethyl)pyrrolidine (200% mol) in dichloromethane to give an amide, 4: FIDA1. In order to use a smaller amount of pyrrolidine base, the synthesis of 6:FIDA2 was performed by making an activated ester of acid 5 with ethyl chloroformate in the presence of triethylamine, followed by addition the mixture of R (+)-N-(4-fluorobenzyl)-2-(aminomethyl) pyrrolidine (100% mol) and triethylamine. This is a one-pot reaction.

Methods analogous to those illustrated in Scheme 1 may be used to prepare other compounds of this invention. Different compounds of Formulas I and II may be prepared by utilizing different starting materials, all of which are either known in the art or readily prepared by methods known in the art.

Compounds of Formula III may be prepared by methods analogous to that illustrated below in Scheme B for the preparation of compound 25.

poses would be with this isotope. Other isotopes which may be used include [121]I (half life of 2 hours). The compounds may be dispersed in pharmaceutically acceptable vehicles, known in the art, such as saline. An effective quantity of the labelled agent is administered to a patient and SPECT imaging methods are used to measure gamma ray emissions therefrom.

The compounds of this invention may be labeled with radioactive iodine by subjecting an intermediate compound of Formula IV, V or VI to an electrophilic radiohalogenation using hydrogen peroxide as the oxidant. This method is illustrated below in Scheme C.

Scheme C

Scheme B

The 4'-bromobenzazepine, 22, is prepared using methods disclosed by Wyrick, S. C., et al., *J. Label. Comod. and Radiopharm.* 22, 189 (1984). The benzazepine 23 may be prepared by N-methylation of 22 with formaldehyde and formic acid. Lithiation of 23 with n-butyllithium at −78° C., to replace the 4'-bromo group, affords the tri-n-butyltin derivative 24. The final product 25 may be prepared by contacting 24 with iodine and then deprotecting the hydroxy group with a suitable deprotecting agent such as boron tribromide or a strong acid. Those skilled in the art will be able to prepare other compounds of Formula III may be made by methods analogous to that illustrated in Scheme B by selecting different starting materials.

For use in SPECT imaging, the compounds of this invention are generally labeled with a radioactive iodine. Although $^{125}$I isotopes are useful for laboratory testing, they will generally not be useful for actual diagnostic purposes because of the relatively long half-life (60 days) and low gamma-emission (30–65 Kev) of [125]I. The isotope $^{123}$I has a half life of thirteen hours and gamma energy of 159 KeV, and it is therefore expected that labeling of ligands to be used for diagnostic pur-

S-(−)FIDA1, 4

11

-continued

Scheme C

12

-continued

Scheme C

The precursors, tributyltin 7 and 9, can be synthesized by heating the mixture of FIDA1 or FIDA 2, bis(tributyltin), tetrakistriphenylpalladium and palladium (II) acetate in triethylamine at 80°–90° overnight. With or without palladium (II) acetate, the reaction produces the same result. The precursor, tributyltin 24, can be prepared as shown above in Scheme B.

For use in PET imaging, the compounds of this invention are generally labeled with a radioactive fluorine, $^{18}F$. The compounds may be dispersed in pharmaceutically acceptable vehicles, known in the art, such as saline. An effective quantity of the labelled agent is administered to a patient and PET imaging methods are used to measure gamma ray emissions therefrom. Labelling of compounds of Formulas II may be accomplished by methods illustrated in Scheme D.

Scheme D

N-benzylation of precursor 15 with [18F]fluorobenzyl iodide 18 in DMF yields the desired fluorinated ligand 19. Further discussion of this type reaction can be found in Haka, M. S., et al., *J. Lab. Comp. Radiopharm* 27, 823–833 (1988) and Mach, R. H., et al., *J. Lab. Comp. Radiopharm.* 30, 154–155 (1991). Precursor 15 may be prepared as illustrated in Scheme E.

Scheme E

Scheme E -continued

15
Precursor of [¹⁸F]R-FIDA2
$[\alpha]_D = 8.4°(c = 1.4, MeOH)$

D-N-Trityl prolinamide, 12, can be synthesized by N-benzylation with triphenyl methyl bromide in the presence of triethylamine. The reduction of 12 to 13 can be performed with sodium borohydride, acetic acid and dioxane as a solvent. The reaction generally gives a low percent yield due to steric hindrance of the trityl group. The amine 13 is easily separated from the starting material by chromatography, and the amide 14 synthesized in the same manner as 6. Addition of hydrogen chloride in ethanol to 14 produces an amide, 15, in good yield.

When amide 14 was actually prepared according to the method illustrated in Scheme E showed optical rotation, $[\alpha]_D = -8.40°$ (c=1.4, MeOH). In a second run of this reaction sequence, the amide 14 was obtained with $[\alpha]_D = 3.30°$ (c=1.96, MeOH). The chromatogram (HPLC, chiralcel OD) showed that 14 from the first run had 100% optical purity, but the second-run 14 showed only 78% enantiomeric excess, indicating the introduction of some racemization during the reduction step of the second run. However, a related example showed that the sodium borohydride-acetic acid complex reduced R-(+)-1-(4-fluorobenzyl)propylamide to R-(+)-(aminomethyl-1-(4-fluorobenzyl)pyrrolidine without racemization. This result was also reported in the literature (Hogberg, T., et al., Acta. Chem. Scand. 43, 660–664 (1989). A similar case of racemization of reduction of S-(−)-1-(4-trityl)prolinamide to S-(−)-2-(aminomethyl)pyrrolidine using lithium aluminium hydride was also reported. Florvall, L., et al., J. Med. Chem. 25, 1280–86 (1982). The bulk of the trityl group may cause racemization of these amide-to-amine reductions.

¹⁸F-labelled compounds of Formulas I and III may be prepared by methods as illustrated in Schemes F and G, respectively.

Scheme F scheme G

F-18 Labeled

Figure 1:
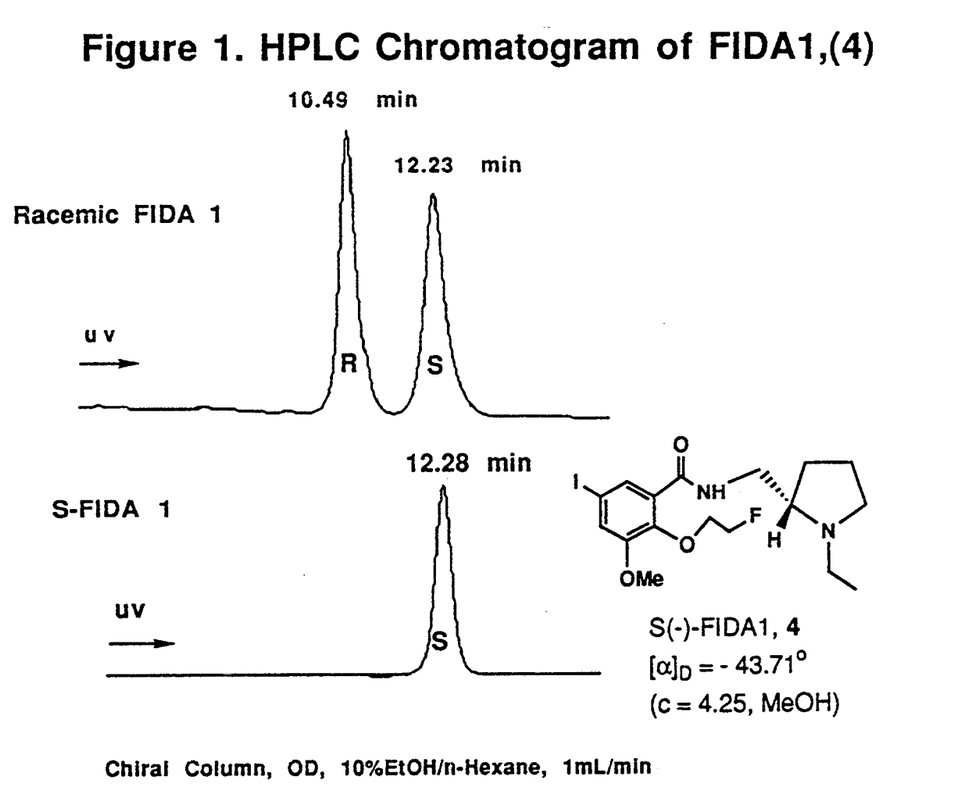
FIG. 1 shows HLPC (high performance liquid chromatography) chromatograms for the racemic mixture and the S-isomer of the compound 2-fluoroethoxy-3-methyl-N-[(1-ethyl-2-pyrrolidinyl)methyl]-5-iodobenzamide.
Figure 2:
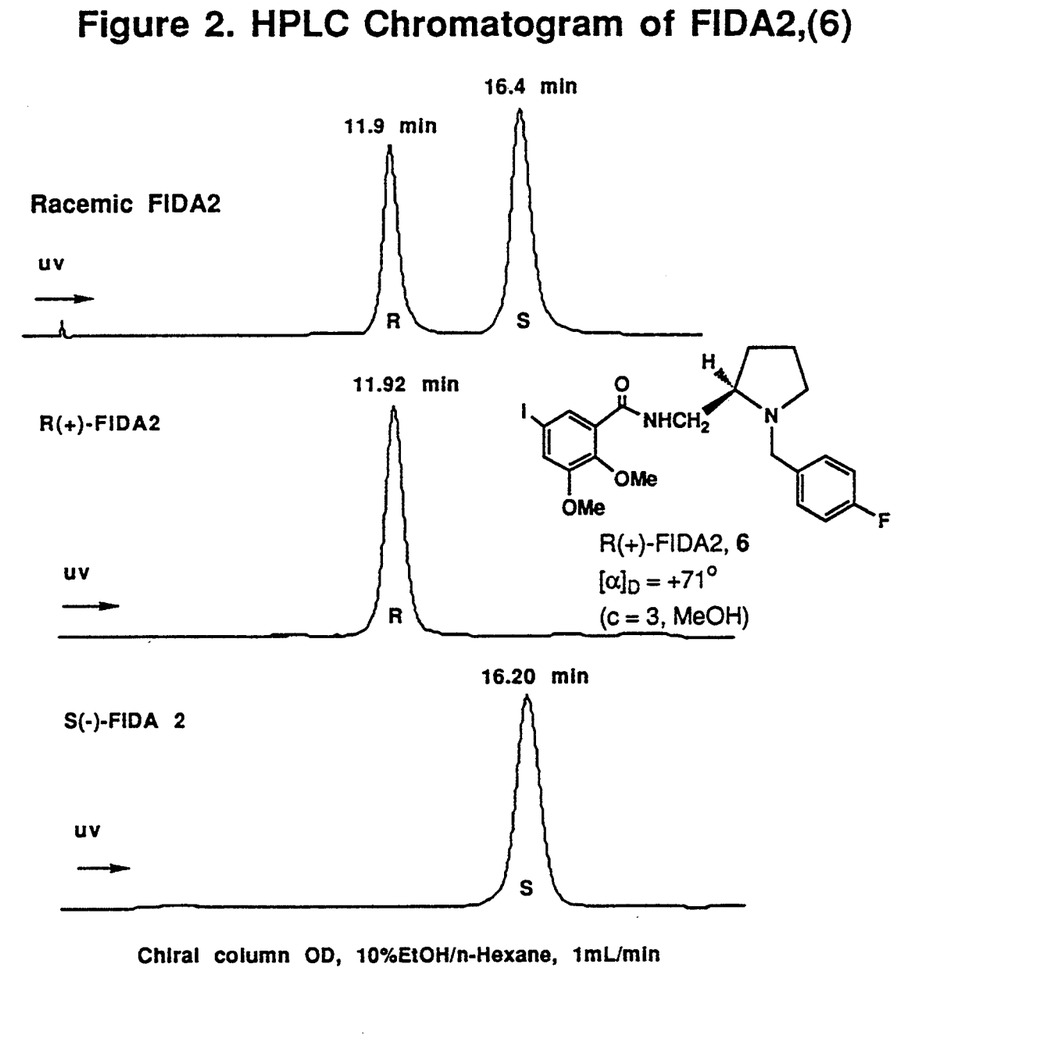
FIG. 2 shows HPLC chromatograms for the racemic mixture, the R-isomer and the S-isomer of the compound 2,3-dimethoxy-N-[(1-(4'-fluorobenzyl)-2-pyrrolidinyl)methyl]-5-iodobenzamide.

Compounds of Formulas I and II can exist as either R— or S— isomers. Optical resolution of the isomers has indicated that the are S-isomers of compounds of Formula I are the active isomers and that the R+ isomers of compounds of Formula II are the active isomers. Optical purity of these compounds may be determined with (high pressure liquid chromatography (HPLC) chiralcel OD). HPLC is a very sensitive method for measurement of optical purity (sensitivity <1%). Chumpradit, S, et al., *J. Med. Chem.* 34, 877–883 (1991).

Preferred compounds of Formula I are those wherein, independently or concurrently, (a) $R_1$ is $(CH_2)_nF$; (b) $R_2$ is $C_1$–$C_5$ alkyl; (c) Y is H and (d) E is I. More preferred compounds of Formula I are those wherein, independently or concurrently, (a) $R_1$ is $CH_2CH_2F$; (b) $R_2$ is $CH_3$; (c) Y is H; and (d) E is I.

Preferred compounds of Formula II are those wherein, independently or concurrently, (a) A is (b) W is F; (c) V is H; (d) $R_1$ is $CH_3$; (e) Z is $OCH_3$; (f) Y is H; and (g) X is I. More preferred compounds of Formula II are those wherein, independently or concurrently, (a) A is (b) W is F and is in the ortho- or para- position; (c) V is H; (d) $R_1$ is $CH_3$; (e) Z is $OCH_3$; (f) Y is H; and (g) X is I.

Preferred compounds of Formula III are those wherein, independently or concurrently, (a) $R_5$ is H; (b) $R_4$ is Cl; (c) X is I; (d) n is 2. More preferred compounds of Formula III are those wherein, independently or concurrently, (a) $R_5$ is H; (b) $R_4$ is Cl; (c) X is I and is in the meta- or para- position; (d) n is 2 and the —$OCH_2CH_2F$ group is in the meta- or para- position.

Specific examples of compounds falling within the scope of this invention are provided in Tables III, IV and V.

TABLE III

I

| $R_1$ | $R_2$ | X | Y |
|---|---|---|---|
| $CH_2CH_2F$ | $CH_3$ | I | H |
| $CH_2CH_2F$ | $CH_3$ | I | $OCH_3$ |
| $CH_2CH_2F$ | $C_2H_5$ | I | H |
| $CH_2CH_2F$ | $C_2H_5$ | I | $OCH_3$ |
| $CH_2CH_2F$ | $C_3H_7$ | I | H |
| $CH_2CH_2F$ | $C_3H_7$ | I | H |
| $CH_2CH_2F$ | $CH_3$ | C=CHI | H |
| $CH_2CH_2CH_2F$ | $CH_3$ | I | H |
| $CH_2CH_2CH_2CH_2$ | $CH_3$ | I | H |
| $CH_2CH_2F$ | $CH_3$ | $CH_2I$ | H |
| $CH_2CH_2F$ | $CH_3$ | $CH_2CH_2I$ | H |
| $CH_2CH_2F$ | $CH_3$ | I | $OC_2H_5$ |
| $CH_3$ | $CH_2CH_2F$ | I | H |
| $CH_3$ | $CH_2CH_2F$ | I | $OCH_3$ |
| $C_2H_5$ | $CH_2CH_2F$ | I | H |
| $C_2H_5$ | $CH_2CH_2F$ | I | $OCH_3$ |
| $CH_3$ | $CH_2CH_2F$ | C=CHI | H |
| $CH_3$ | $CH_2CH_2CH_2F$ | I | H |
| $CH_3$ | $(CH_2)_4F$ | I | H |
| $CH_3$ | $CH_2CH_2F$ | $CH_2I$ | H |
| $CH_3$ | $CH_2CH_2F$ | $CH_2CH_2I$ | H |

TABLE IV

II where A is

TABLE IV-continued (1)

(2)

(3)

| R1 | X | Y | Z | A | V | W |
|---|---|---|---|---|---|---|
| CH3 | I | H | OCH3 | 1 | H | F |
| CH3 | I | OCH3 | OCH3 | 1 | H | F |
| CH3 | I | H | H | 1 | H | F |
| CH3 | I | OCH3 | OCH3 | 1 | H | F |
| CH3 | CCHI | H | OCH3 | 1 | H | F |
| CH3 | CCHI | OCH3 | OCH3 | 1 | H | F |
| CH3 | CCHI | H | H | 1 | H | F |
| CH3 | CCHI | OCH3 | OCH3 | 1 | H | F |
| CH3 | CH2I | H | OCH3 | 1 | H | F |
| CH3 | CH2I | OCH3 | OCH3 | 1 | H | F |
| CH3 | CH2I | H | H | 1 | H | F |
| CH3 | CH2I | OCH3 | OCH3 | 1 | H | F |
| CH3 | I | H | OCH3 | 1 | H | CH2F |
| CH3 | I | H | OCH3 | 1 | OH | F |
| CH3 | I | H | OCH3 | 1 | OCH3 | F |
| CH3 | I | H | OCH3 | 1 | CH3 | F |
| CH3 | I | H | OCH3 | 2 | H | F |
| CH3 | I | OCH3 | OCH3 | 2 | H | F |
| CH3 | I | H | H | 2 | H | F |
| CH3 | I | OCH3 | OCH3 | 2 | H | F |
| CH3 | CCHI | H | OCH3 | 2 | H | F |
| CH3 | CCHI | OCH3 | OCH3 | 2 | H | F |
| CH2 | CCHI | H | H | 2 | H | F |
| CH3 | CCHI | OCH3 | OCH3 | 2 | H | F |
| CH3 | CH2I | H | OCH3 | 2 | H | F |
| CH3 | CH2I | OCH3 | OCH3 | 2 | H | F |
| CH3 | CH2I | H | H | 2 | H | F |
| CH3 | CH2I | OCH3 | OCH3 | 2 | H | F |
| CH3 | I | H | OCH3 | 2 | H | CH2F |
| CH3 | I | H | OCH3 | 2 | OH | F |
| CH3 | I | H | OCH3 | 2 | OCH3 | F |
| CH3 | I | H | OCH3 | 2 | CH3 | F |
| CH3 | I | H | OCH3 | 3 | H | F |
| CH3 | I | OCH3 | OCH3 | 3 | H | F |
| CH3 | I | H | H | 3 | H | F |
| CH3 | I | OCH3 | OCH3 | 3 | H | F |
| CH3 | CCHI | H | OCH3 | 3 | H | F |
| CH3 | CCHI | OCH3 | OCH3 | 3 | H | F |
| CH3 | CCHI | H | H | 3 | H | F |
| CH3 | CCHI | OCH3 | OCH3 | 3 | H | F |
| CH3 | CH2I | H | OCH3 | 3 | H | F |
| CH3 | CH2I | OCH3 | OCH3 | 3 | H | F |
| CH3 | CH2I | H | H | 3 | H | F |
| CH3 | CH2I | OCH3 | OCH3 | 3 | H | F |
| CH3 | I | H | OCH3 | 3 | H | CH2F |
| CH3 | I | H | OCH3 | 3 | OH | F |
| CH3 | I | H | OCH3 | 3 | OCH3 | F |
| CH3 | I | H | OCH3 | 3 | CH3 | F |

TABLE V

III

| R4 | R5 | X | n |
|---|---|---|---|
| Cl | H | I | 2 |
| Cl | H | C=CHI | 2 |
| Cl | H | CH2I | 2 |
| Cl | H | I | 1 |
| Cl | H | C=CHI | 1 |
| Cl | H | CH2I | 1 |
| Cl | CH3 | I | 2 |
| Cl | CH3 | C=CHI | 2 |
| Cl | CH3 | CH2I | 2 |
| OH | Cl | I | 2 |
| CH3 | Cl | I | 2 |

The preparation and testing of the compounds of this invention are discussed in more detail in the following examples which are not intended to limit the scope of this invention.

In these examples, NMR were recorded on a Varian EM 360A, a Bruker WM-250 (250 MHz) or a Bruker AM 500 (500 MHz) spectrometer. The chemical shifts were reported in ppm downfield from an internal tetramethylsilane standard. Infrared spectra were obtained with a Mattson Polaris FT-IR spectrophotometer. Melting points were determined on a Meltemp apparatus and are reported uncorrected. HPLC was performed on model Rabbit HP from Rainin Instrument Co. Inc. (Emeryville, Calif.) using chiral column (chiralcel-OD, 4.1×250 mm), Diacel Inc. (Los Angeles, Calif.). Optical rotation of compounds was measured on a Perkin-Elmer 243B polarimeter. Mass spectra were performed on the masspectrometer VG 70-70 HS with chemical ionization (Cl), using methane or ammonia gas. Elemental analyses were performed by Atlantic Microlabs, Inc., of. Norcross, Ga., and were within 0.4% of the theoretical values.

Materials: Dichloromethane was refluxed and distilled from calcium hydride. D-Dopa, L-Dopa, 3-methoxysalicyclic acid, oxalyl chloride and ethyl chloroformate were purchased from Aldrich (Milwaukee, Wis.) and used without further purification. S(—)-N-ethyl-2-(aminomethyl)pyrrolidine was obtained from the resolution of RS-N-ethyl-2-(aminomethyl)pyrrolidine according to the published procedure. Kung, H. F., et al., J. Med. Chem. 31, 1039–1043 (1988). R(+)- and S(—)-2-aminomethyl-1-(4-fluorobenzyl)pyrrolidine were synthesized according to the literature. Hogberg, T., et al., Acta. Chem. Scand. 43, 660-664 (1989).

EXAMPLE 1

Methyl-5-iodo-3-methoxysalicylate (1)

The esterification of 3-methoxysalicylic acid was performed according to the literature. Bishop, J. E., et al., *J. Med. Chem.* 34, 1612–1624 (1991). The ester product (1.68 g, 9.20 mmol) was dissolved in methanol (35 mL). Sodium iodide (1.38 g, 9.20 mmol) and sodium hydroxide (0.34 g, 9.2 mmol) were added, and the solution was cooled to 0° C. To this solution aqueous sodium hypochlorite (17.25 g, 5% naClO) was added dropwise. The colorless slurry mixture was stirred for 1 h at 0°–3° C., then treated with 10% aqueous sodium thiosulfite. The mixture was adjusted to pH 7 using 5% aqueous HCl. Ether (50 mL) was added and the layers were separated. The ether layer was washed with brine and dried over anhydrous sodium sulfate. After the ether was evaporated, the crude orange solid was purified by column chromatography (silica gel, CHCl$_3$) to obtain 1.2 g (43%) of the iodoproduct; m.p. 104° C. (lit[4] 110°–112° C.). The spectra were the the same as those published in the literature. Yue, E. W., et al., *J. Org. Chem.* 56, 5451–5456 (1991).

EXAMPLE 2

2-Fluoroethoxy-5-iodo-3-methoxy Benzoic Acid (3)

Compound 1 (0.943 g, 3.66 mmol) was dissolved in dried acetone (40 mL), and potassium carbonate (1.5 g, 10.86 mmol) was added, followed by 1-bromo-2-fluoroethane. The mixture was refluxed with stirring for 48 h. Acetone was evaporated and the residue was dissolved in dichloromethane, washed several times with water, and dried over anhydrous sodium sulfate. Dichloromethane was evaporated under reduced pressure. The crude product was purified by column chromatography (silica gel, ethyl acetate: petroleum ether=20/80) to obtain 0.9 g (86%) of compound 2. The ester 2 was hydrolized to the acid 3 based on the published procedure Kung, H. F., et al., *J. Med. Chem.* 31, 1039–1043 (1988) to provide a white solid in 79% yield. m.p. 125°–126° C. FT-IR (KBr) λ3450 (br, OH), 1740 (strong, CO). $^1$h NMR (CDCl$_3$) δ8.05 (d, 1H), 7.39 (d, 1H), 4.78 (m, 1H), 4.68 (m, 1H). 4.52 (m, 1H), 4.46 (m, 1H), 3.88 (s, 3H). Anal. Calcd. (CI, high resolution spectrum) for C$_{10}$H$_{14}$O$_4$IF, (M+H) 339.96, found 339.96.

EXAMPLE 3

(S)-(−)-2-Fluoroethoxy-3-methyl-N-[(1-ethyl-2-pyrrolidinyl)methyl]-5-iodobenzamide: FIDA (4)

The acid 3 (0.05 g, 1.47 mmol) was dissolved in dichloromethane (12 mL). The reaction solution was cooled to 0° C. and oxalyl chloride (0.45 mL, 5.1 mmol) was added, followed by DMF (30 μL). The solution was stirred at 0° C. for 30 min, concentrated in a rotary evaporator (bath temperature ~30° C.). The slightly yellow solid of the acid chloride was redissolved in dichloromethane (12 mL). To this acid chloride solution the amine S(−)-N-ethyl-2-(aminoethyl)pyrrolidine (0.30 g, 2.9 eq) was added. After stirring at room temperature for 20 min, the solvent was evaporated under reduced pressure. The residue was redissolved in dichloromethane, washed with 5% NaHCO$_3$, dried over anhydrous sodium sulfate, and filtered; the solvent was removed under reduced pressure. The crude oil product was purified by column chromatography (silica gel, CHCl$_2$: MeOH, 90/10) to afford 4 (0.052 g, 81%) as an oil. [α]$_D$=43.71° (c=4.25, MeOH). MS, M/z 451 (M+H) FT-IR (neat) λ3400 (br, NH of amide) 1660 (strong, CO). $^1$H NMR (CDCl$_3$) δ8.04 (br, 1H), 8.01 (d, 1H, J=1.84 hz), 7.27 (D, 1H, J−1.90 Hz), 4.70 (m, 1H), 4.60 (m, 1H), 4.32–4.28 (M, 2H), 3.86 (s, 3H), 3.75 (dddd, 1H), 3.27 (dt, 1H), 3.18 (m, 1H), 2.89 (sext,. 1H), 2.70 (m, 1H), 2.26 (sext., 1H), 2.18 (q, 1H), 1.89 (M, 1H), 1.71 (m, 2H), 1.62 (m, 1H), 1.11 (t, 3H). $^{13}$C NMR (CDCl$_3$) δ163.84, 152.90, 145.62, 131.79, 128.85, 123.95, 87.42, 82.72, 81.36, 77.25, 76.99, 76.74, 72.62, 72.47, 62.74, 59.32, 53.47, 50.61, 48.28, 41.77, 28.35, 22.51, 13.53. Anal. calcd. for C$_{25}$H$_{36}$IO$_9$N$_2$F (tartrate salt) C,H,N: Optical purity=100%, retention time 12.28 min (chiralcel OD, 10%/ethano/hexane, 1 mL/min)

EXAMPLE 4

5-Iodo-2,3-dimethoxy Benzoic Acid (5)

The procedure utilized was the same as that used in the synthesis of 2, except methyl iodide was used as an O-alkylation agent. After work-up and purification, the methyl-5-iodo-2,3-dimethoxy benzoate was obtained in 96% yield. The final compound 5 was obtained in 81% yield. m.p. 118°–119° C. (lit[3] 117°–118° C.). The spectra are the same as those published in the literature. Yue, E. W., et al., *J. Org. Chem.* 56, 5451–5456 (1991).

EXAMPLE 5

S-(−)-2-Fluoromethoxy-3-methyl-N-[1-ethyl-2-(pyrrolidinyl)methyl]-5-tri-n-butyltin Benzamide (7)

The FIDA 1, 4 (0.52 g. 1.19 mmol) was dissolved in triethylamine (10 mL). Palladium (0) acetate (0.02 g, 089 mmol) and tetrakistriphenyl phosphine palladium (0) (0.045 g, 0,039 mmol) were added, followed by bis(tributyltin) (1.04 mL, 2.05 mmol). The mixture was heated to 95°–100° C. (oil bath) for 2.5 h. The black reaction mixture was filtered and the black solid washed with triethyl amine. The filtrate was evaporated under reduced pressure (temperature <50° C.). The oil residue was purified by column chromatography (silica gel, EtOAc:MeOH:NH$_4$OH, 90/10/1) to afford a clear oil of 7 (0.31 g, 42%). FT-IR (neat) δ3400 (C=O), 3000–2800 (very strong, nonaromatic CH), 1670 (strong, C=O). $^1$H NMR (CDCl$_3$) δ8.08 (br, 1H), 7.74 (s, 1H), 7.06 (s, 1H, 4.76 (m, 1H), 4.66 (m, 1H), 4.35–4.26 (M, 2H), 3.79 (s, 3H), 3.77 (dddd, 1H), 3.28 (br, 1H), 3.18 (br, 1H), 2.91 (br, 1H), 2.30 (br, 1H), 2.19 (br, 1H), 1.90 (br, 1H), 1.70 (br, 2H), 1.31 (t, 3H), 1.540.84 (m, 27H), $^{13}$C NMR (CDCl$_3$) δ166.28, 151.63, 145.76, 138.08, 130.50, 126.08, 122.96, 82.95, 81.59, 77.23, 76.97, 76.72, 72.47, 72.32, 64.10, 56.06, 53.52, 49.12, 41.50, 30.74, from 29.0−9.69 (18 peaks). Anal. calcd. for C$_{29}$H$_{51}$FN$_2$O$_3$Sn: C,H,N.

EXAMPLE 6

R(+)-2,3-dimethoxy-N-[(1-(4′-fluorobenzyl)-2-pyrrolidinyl)methyl]-5-iodobenzamide: FIDA 2(6)

The acid 3 (0.262, 0.84 mmol) was dissolved in dichloromethane (6 mL), and the solution was cooled to 0° C. To this acid solution, triethylamine (0.15 mL, 0.11 mmol) and ethyl chloroformate (0.1 mL, 0.1 mmol) in dichloromethane (2 mL) was added during stirring at 0° C. After 1 h a mixture of R(+)-2-aminomethyl-1-(4-fluorobenzyl)pyrrolidine[2] (0.208 g, 0.1 mmol) and triethylamine (0.15 mL, 0.11 mmol) in dichloromethane (5 mL) was added to the reaction solution. The mixture was stirred at 0° C. for another 1.5 h; the solvent was evaporated under reduced pressure. The residue was redissolved in dichloromethane, washed 3 times with water, and dried over anhydrous sodium sulfate. The solvent was rotoevaporated, and the crude product was purified by column chromatography (silica gel, $CH_2Cl_2$:MeOH:$NH_4OH$, 95/5/1) to obtain 0.348 g (82%) of FIDA 2, 6. $[\alpha]_D = +71°$ (c=3, MeOH), MS, M/z, 516 (M+). FT-IR (neat) λ3399 (medium, C=O), 1660 (strong, C=O). $^1H$ NMR ($CDCl_3$) δ8.35 (br, 1H), 7.68 (d, 1H0, 7.26 (m, 2H), 6.96 (m, 3H), 3.97 (d, 1H), 3.88 (S, 3H), 3.84 (s, 3H), 3.81 (dd, 1H), 3.31 (d, 1H), 3.24 (d, 1H), 2.91 (br, 1H), 2.75 (br, 1H), 2.17 (br, 1H), 1.94 (m, 1H), 1.68 (br, 2H), 1.59 (s, 1H). Anal. calcd. for $C_{25}H_3IO_9N_2F$ (tartrate salt): C, H, N. Optical purity—100%, retention time 11.92 min (chiralcel OD, 10% ethanol/hexane, 1 mL/min)

EXAMPLE 7

R(+)-2,3-dimethoxy-N-[(1-(4'-fluorobenzyl)-2-pyrrolidinyl)methyl]-5-trin-butyltin Benzamide (9)

Using the same procedure as for the synthesis of compound 7, 45% of the desired product was obtained. $^1H$ NMR ($CDCl_3$) 8.30 (br, CO), 7.73 (d, 1H, J—1.08 Hz), 7.22 (m, 2H), 7.04 (d, 1H, J—0.97 Hz), 6.90 (m, 2H), 2.94 (d, 1H), 3.82 (S, 3H), 3.79 (m, 1H), 3.78 (s, 3H), 3.20 (dt, 1H), 3.17 (d, 1H), 2.85 (br, 1H), 2.71 (br, 1H), 2.11 (q, 1H), 2.09 (m, 1H), 1.64 (m, 3H), 1.48–0.80 (m, 27H). Anal. calcd. for $C_{38}H_{51}O_3N_2FSn$: C, H, N.

EXAMPLE 8

R-(−)-2,3-dimethoxy-N-(2-pyrrolidinyl)methyl-5-iodobenzamide (15)

R-(+)-prolinamide, 11, was converted to R-(+)-N-trilyl prolinamine, 12, using the procedure published in the literature (Hogberg, T., et al., *Acta. Chem. Scand.* 43, 660–664 (1989)), but using trityl bromide instead of trityl chloride. Compound 12 was reduced to R-(−)-B-trityl prolinamide, 13, using sodium borohydride, acetic acid and dioxane. (Florvall, L., et al., *J. Med. Chem.* 25, 1280-86 (1982). The amine 12 was condensed with the acid 5 on the same basis as the synthesis of compound 6, to afford N-trityl benzamide (14). Compound 14 was treated with hydrogen chloride in ethanol to give 15 in 65% yield. $[\alpha]_D = -8.4°$ C. (C=1.4, MeOH), m.p. 200°–202° C. (hydrochloride salt), FT-IR (KBr) λ3390 (br, NH), 3300 (sharp, NH (amide)), 1660 (strong, C=O). $^1H$ NMR ($CDCl_3$) δ8.29 (br, NH), 7.95 (d, 1H, J=1.95 Hz), 7.25 (d, 1H, J=1.99 Hz), 3.90 (s, 3H), 3.84 (s, 3H), 3.57 (m, 1H), 3.47 (m, 1H), 3.39 (m, 1H), 3.00 (m, 2H), 1.93 (m, 1H), 1.83 (m, 1H), 1.78 (m, 1H), 1.50 (m, 1H). Anal. calcd. for $C_{14}H_{20}ClIO_3N$: C, H, N. Optical purity=100% retention time 8.75 mL (chiralcel OD, 10% ethanol/hexane, 1 mL/min).

EXAMPLE 9

Iodoradiolabeling

Aqueous hydrogen peroxide (50 μL, 3% w.v) was added to a mixture of 50 μL of compound 7 or 9 (1 mg/mL of EtOH(, 50 μL of 0.1 H NCI, and 5 μL of [$^{125}$I] sodium iodide (2–3 mCi, carrier-free, Sp. act. 2,200 Ci/mmol) in a sealed vial. The reaction was allowed to proceed at 23° C. for 30 min, after which it was terminated by the addition of 0.1 mL of sodium bisulfite (300 mg/mL). The reaction mixture was neutralized via the addition of saturated $NaHCO_3$ solution and then extracted with ethyl acetate (3×1 mL). The combined organic layers were passed through an anhydrous sodium sulfate column (0.2 cm×5 cm) and evaporated to dryness by a stream of nitrogen. The residue was dissolved in 100% ethanol (50–100 μL), and the desired product, [$^{125}$I]FIDA (8 or 10), was isolated from unreacted 7 or 9 and a small amount of unknown radioactive impurities by HPLC, using a reverse-phase column (PRP-1, Hamilton, Inc.) and an isocratic solvent of 90% acetonitrile −10% pH 7.0 buffer (5 mM, 3,3-dimethylglutaric acid). The appropriate fractions were collected, condensed, and reextracted with ethyl acetate (1×3 mL). The solution containing the no-carrier-added product was condensed to dryness and redissolved into 100% ethanol (purity >99%, overall yield 75%). After dilution with saline, this agent was used for the in vivo and in vitro studies.

EXAMPLE 10

$^{18}F$-Radiolabeling

[$^{18}$F]18 was prepared by N-alkylation of 15 with [$^{18}$F]4-fluorobenzyl iodide using a modification of the published method. Haka, M. S., et al., *J. Lab. Comp. Radiopharm,* 27, 823-833 (1988). No-carrier-added aqueous [$^{18}$F]fluoride (115 mCi) was prepared by the University of Pennsylvania JSW BC 3015 cyclotron via the $^{18}O(p,n)$ $^{18}F$ nuclear reaction on a small volume enriched water (98%) target. The target material was passed through an AG1-X8 (bioRad) anion exchange resin (hydroxide form, 20–30 mg) and converted into [$^{18}$F]CsF by elution with 0.5 mL of aqueous cesium carbonate (4 mg/mL) into a glass reaction vessel. The water was removed in vacuo at 90° C. under a stream of nitrogen and the [$^{18}$F]CsF was redissolved in a solution of 200 μL DMSO/7 μL water. A mixture of 16 in 100 mL DMSO was added and the reaction mixture was heated at 120° C. for 10 min. Mach, R. H., et al., *J. Lab. Comp. Radiopharm.* 30, 154–155 (1991). Following Sep-pak purification, the [$^{18}$F]4-fluorobenzaldehyde, 17, was converted to [$^{18}$F]4-fluorobenzyliodide, 18, according to the published method. Haka, M. S., et al., *J. Lab. Comp. Radiopharm* 27, 823-833 (1988). N-alkylation of 15 was performed by heating a mixture of 15 and 19 in 500 mL DMF at 90° C. for 10 min. The crude product was purified by C18 reversed-phase HPLC (0.1M ammonium formate/methanol, 20:80) to give 6.8 mCi of [$^{18}$F]19 (10% radiochemical yield decay corrected to SOS). The total synthesis time was 130 min and the specific activity of [$^{18}$F]19 was ~800 mCi/mmol. The radiochemical purity was >99%.

EXAMPLE 11

Biodistribution in rats

Male Sprague-Dawley rats (225–300 g), which were allowed free access to food and water, were used for the vivo biodistribution study. While under halothane anesthesia, 0.2 mL of a saline solution containing [$^{125}$I]-FIDA 8 or 10 (8–10 μCi) was injected daily into the femoral vein of rats, and they were sacrificed at various time points postinjection by cardiac excision under halothane anesthesia. The organs of interest were removed and weighed and the radioactivity was counted with a Beckman gamma automatic counter (Model 4000). The percent dose per organ was calculated by a comparison of the tissue counts to suitably diluted aliquots of the injected material. Total activities of blood and muscle were calculated under the assumption that they were 7% and 40% of the total body weight, respectively.

Regional brain distribution in rats was obtained after an injection of [$^{125}$I]FIDA 8 or 10. By dissecting, weighing, and counting samples from different brain regions (cortex, striatum, hippocampus, and cerebellum), the percent dose/gram of sample was calculated by comparing the sample counts with the count of the diluted initial dose. The uptake ratio of each region was obtained by dividing the percent dose/gram of each region by that to the cerebellum.

EXAMPLE 12

In Vitro Binding

Rat tissue homogenates were prepared as described previously. Murphy, R. A., et al., *J. Med. Chem.* 33, 171-178 (1990). The binding assays were performed by incubating 50 μL of tissue preparations containing 40-60 μg of protein with appropriate amounts of $^{125}$I-labeled ligand and competitors in a total volume of 0.2 mL of the assay buffer. After an incubation period of 15 min at 37° C. (with stirring), the samples were rapidly filtered in a cell harvester (Brandel M-24R) under vacuum through Whatman GF/B glass-fiber filters pretreated with 0/2% protamine base and washed with 3×5 mL of cold (4° C.) 50 mM Tris-HCI buffer, pH 7.4. The nonspecific binding was obtained in the presence of 10 μM (+)butaclamol. The filters were counted in a γcounter (Beckman 5500) at an efficiency of 70%. Both Scatchard and competition experiments were analyzed with the iterative nonlinear least squares curve-fitting program LIGAND. Munson, P. J., et al., *Anal Biochem.* 107, 220 (1980) .

Competition study with various types of receptor ligands indicated that [$^{125}$I] of FIDA1 and FIDA2 specifically binds to the dopamine D2 receptor with great selectivity. See Tables VI-A and VI-B.

TABLE VI-A

Inhibition Constants of Compounds on $^{125}$I-FIDA-1 Binding to Rat Striatal Membranes

| Compounds | K$_i$ (nM) | Receptor Type |
|---|---|---|
| spiperone | 0.02±0.003 | D-2 antagonist |
| eticopride | 0.014±0.002 | D-2 antagonist |
| (+) butacamol | 1.05 ±0.12 | D-1 & D-2 |
| raclopride | 2.31 ±0.43 | D-2 antagonist |
| WB 4101 | 33.1±1.5 | α-1 |
| SCH23390 | 460±38 | D-1 |
| quipirole | 2053±410 | DA agonist |
| dopamine | 1437±175 | DA agonist |
| atropine | >10,000 | cholinergic |
| Naloxone | >10,000 | opiate |
| 5-HT | >5,000 | 5-HT |
| (±) propranolol | >10,000 | β-adrenergic |

TABLE VI-B

Inhibition Constants of Compounds on $^{125}$I-FIDA-2 Binding to Rat Striatal Membranes

| Compounds | K$_i$ (nM) | Receptor Type |
|---|---|---|
| eticopride | 0.06±0.005 | D-2 antagonist |
| spiperone | 0.03±0.01 | D-2 antagonist |
| (+) butacamol | 0.40±0.02 | D-2 & D-1 |
| raclopride | 5.0±0.8 | D-2 antagonist |
| WB4101 | 23.3±2.2 | α-1 adrenergic |
| yohimbine | 505±70 | α-2 adrenergic |
| quipirole | 8000±1600 | DA agonist |
| SCH233990 | 536±33 | D-1 antagonist |
| dopamine | 5268±1000 | DA agonist |
| naloxone | >10,000 | opiate |
| atropine | >10,000 | cholinergic |

TABLE VI-B-continued

Inhibition Constants of Compounds on $^{125}$I-FIDA-2 Binding to Rat Striatal Membranes

| Compounds | K$_i$ (nM) | Receptor Type |
|---|---|---|
| 5-HT | >3,000 | 5-HT |

EXAMPLE 13

In Vivo Biodistribution in Rats

FIDA1: After an iv injection, [$^{123}$I]FIDA1 (8) showed moderate brain uptake in rate. At later time points the brain uptake decreased: 1 h after injection, a large portion of the radioactivity has washed out from the brain (0.05% dose/organ). The liver uptake remained high for the first 30 min and rapidly washed out at 1 h postinjection.

With a brain regional dissection technique, the striatum/cerebellum (ST/CB) ratio (target to nontarget ratio) dramatically increased with time: 8.26, 29.3 and 60.7 at 30, 60 and 10 min respectively. This type of profound increase in target to nontarget ratio vs. time was not observed for the other two regions, hippocampus and cortex. These results suggest that in regions with nonspecific association, i.e. regions low in dopamine receptors, the agent is washed out rapidly, whereas the striatum (rich in dopamine receptors) shows prolonged retention.

FIDA2: [$^{123}$I]FIDA2 exhibited better brain uptake in rats than [$^{123}$I]FIDA1 (0.98% dose/organ). At 1 h after injection with [$^{123}$I]FIDA1, the radioactivity had washed out from the brain (0.10% dose/organ). High initial uptake in the liver was also observed, but the clearing of the radioactivity was slower than it was for [$^{123}$I]FIDA1. The ST/CB ratio showed a gradual increase, from 1.2% does/organ at 2 min to 25.2% dose/organ at 120 min. The studies (data not shown) on ex vivo autoradiography of these compounds also confirm the high striatal uptake and low cerebellar activity.

Since [$^{123}$I]FIDA2 showed higher brain uptake than [$^{123}$I]FIDA1, the compound was first chosen for $^{18}$F labeling for PET imaging in monkeys.

What is claimed is:

1. A compound selected from the group consisting of compounds of formulas I, II and III:

where
X is selected from the group consisting of I, —(CH$_2$)$_n$I and —(CH$_2$)$_q$C≡CHI;
n is an integer of from one to six;
q is zero or an integer of from one to four;
Y is selected from the group consisting of H and OR$_3$;
Z is selected from the group consisting of H and OR$_2$
or Z and OR$_1$ can be taken together to form a ring where
m is an integer of from two to four;
R$_1$, R$_2$ and R$_3$ are independently selected from the group consisting of H, C$_1$-C$_5$ alkyl, and —(CH$_2$)$_n$F; provided that, in compounds of Formula I, at least one of R$_1$, R$_2$ and R$_3$ is —(CH$_2$)n$_F$, and that, in Compounds of Formula II, at least one of —OR$_1$, Y and Z is —O(CH$_2$)$_n$F;
R$_4$ is selected from the group consisting of OH, Cl and CH$_3$;
R$_5$ is selected from the group consisting of H, Cl and OCH$_3$, provided that when R$_4$ is Cl, then R$_5$ is H or CH$_3$, and that when R$_5$ is H or CH$_3$, then R$_4$ is Cl;
A is selected from the group consisting of and s is an integer of from 1 to 3;
W is selected from the group consisting of F and (CH$_2$)$_n$F; and
V is selected from the group consisting of H, OH, OCH$_3$, CH$_3$ and I.

2. A compound of claim 1 which has Formula I.
3. A compound of claim 2 wherein R$_1$ is —(CH$_2$)$_n$F.
4. A compound of claim 3 wherein n is 2.
5. A compound of claim 2 wherein R$_2$ is C$_1$ to C$_5$ alkyl.
6. A compound of claim 5 wherein R$_2$ is CH$_3$.
7. A compound of claim 2 where Y is H.
8. A compound of claim 2 where X is I.
9. A compound of claim 2 where R$_1$ is —CH$_2$CH$_2$F and R$_2$ is CH$_3$.
10. A compound of claim 9 where Y is H and X is I.
11. A compound of claim 1 which has Formula II.
12. A compound of claim 11 where A is 13. A compound of claim 12 where W is F and V is H.
14. A compound of claim 13 where W is selected from the group consisting of para-F and ortho-F.
15. A compound of claim 11 where R$_1$ is CH$_3$.
16. A compound of claim 11 where Z is OCH$_3$.
17. A compound of claim 11 where Y is H.
18. A compound of claim 11 where X is I.
19. A compound of claim 13 where R$_1$ is CH$_3$ and Z is OCH$_3$.
20. A compound of claim 18 where Y is H and X is I.
21. A compound of claim 1 which has Formula III.
22. A compound of claim 21 where R$_5$ is H.
23. A compound of claim 21 where R$_4$ is Cl.
24. A compound of claim 21 where X is I.
25. A compound of claim 21 where n is 2.
26. A compound of claim 21 where R$_5$ is H and R$_4$ is Cl.
27. A compound of claim 21 where X is I and n is 2.
28. A compound of claim 27 where X is para-I and the —OCH$_2$CH$_2$F is in the meta-position.
29. A compound of claim 27 where X is meta-I and the —OCH$_2$CH$_2$F is in the para-position.
30. A compound of claim 28 where R$_5$ is H and R$_4$ is Cl.
31. A compound of claim 28 where R$_5$ is H and R$_4$ is Cl.

32. A compound of a formula selected from the group consisting of

IV

V

VI where
R₁, R₂, Y, Z, A, R₄ and R₅ are as defined in claim 1 and where R₆ is a C₁-C₃ alkyl group.

33. A compound of the formula

VII where
Y' is selected from the group consisting of H and OR₃'; and R₆ is a C₁-C₄ alkyl group;
R₁', R₂' and R₃' are independently selected from the group consisting of H, C₁-C₅ alkyl and —(CH₂)-ₙOTs where Ts is tosylate, provided that at least one of R₁', R₂' and R₃' is —(CH₂)ₙOTs.

34. A compound of the formula

VIII where
Y' is selected from the group consisting of H and OR₃';
Z' is selected from the group consisting of H and OR₂' or Z' and OR₁' can be taken together to form a ring where
m is an integer of from two to four;
R₁', R₂' and R₃' are independently selected from the group consisting of H, C₁-C₅ alkyl and —(CH₂)-ₙOTs where Ts is tosylate, provided that at least one of R₁', Y' and Z' is —O(CH₂)ₙ OTs where Ts is tosylate; and
A' is selected from the group consisting of 35. A compound of the formula

IX where
R₄, R₅, and X are defined as in claim 1, and where Ts is tosylate.

* * * * *